(12) United States Patent
Beck et al.

(10) Patent No.: US 7,494,485 B2
(45) Date of Patent: Feb. 24, 2009

(54) FLUIDIC INTERVENTIONAL DEVICE AND METHOD OF DISTAL PROTECTION

(75) Inventors: Robert C. Beck, St. Paul, MN (US); Hans Mische, St. Cloud, MN (US)

(73) Assignee: Sprite Solutions, St. Paul, MN (US)

( * ) Notice: Subject to any disclaimer, the term of this patent is extended or adjusted under 35 U.S.C. 154(b) by 1337 days.

(21) Appl. No.: 10/050,978

(22) Filed: Jan. 18, 2002

(65) Prior Publication Data

US 2002/0120226 A1    Aug. 29, 2002

Related U.S. Application Data

(63) Continuation-in-part of application No. 09/995,303, filed on Nov. 27, 2001, which is a continuation of application No. 09/459,225, filed on Dec. 10, 1999, now abandoned, said application No. 10/050,978 is a continuation-in-part of application No. 09/637,529, filed on Aug. 11, 2000.

(60) Provisional application No. 60/292,614, filed on May 22, 2001, provisional application No. 60/262,866, filed on Jan. 18, 2001, provisional application No. 60/293,856, filed on May 25, 2001, provisional application No. 60/296,592, filed on Jun. 7, 2001.

(51) Int. Cl.
*A61M 29/00* (2006.01)
*A61M 31/00* (2006.01)

(52) U.S. Cl. .................... 604/509; 604/96.01

(58) Field of Classification Search ............ 604/96.01, 604/101.01, 22, 508, 509, 102.02, 102.01, 604/103.05, 102.03, 152, 507; 606/191–194
See application file for complete search history.

(56) References Cited

U.S. PATENT DOCUMENTS

| | | | | |
|---|---|---|---|---|
| 5,947,985 A | * | 9/1999 | Imran | 606/159 |
| 6,022,336 A | * | 2/2000 | Zadno-Azizi et al. | 604/96 |
| 6,454,741 B1 | * | 9/2002 | Muni et al. | 604/96.01 |

* cited by examiner

*Primary Examiner*—Manuel A Mendez
(74) *Attorney, Agent, or Firm*—Beck & Tysver, PLLC

(57) ABSTRACT

A catheter for injecting and extracting fluids to interact with material at a treatment site in the body.

17 Claims, 9 Drawing Sheets

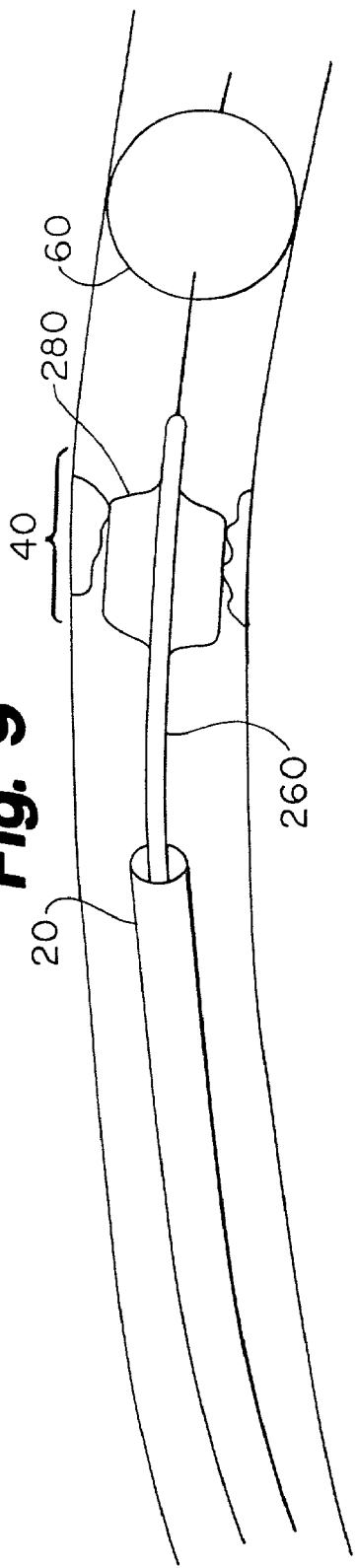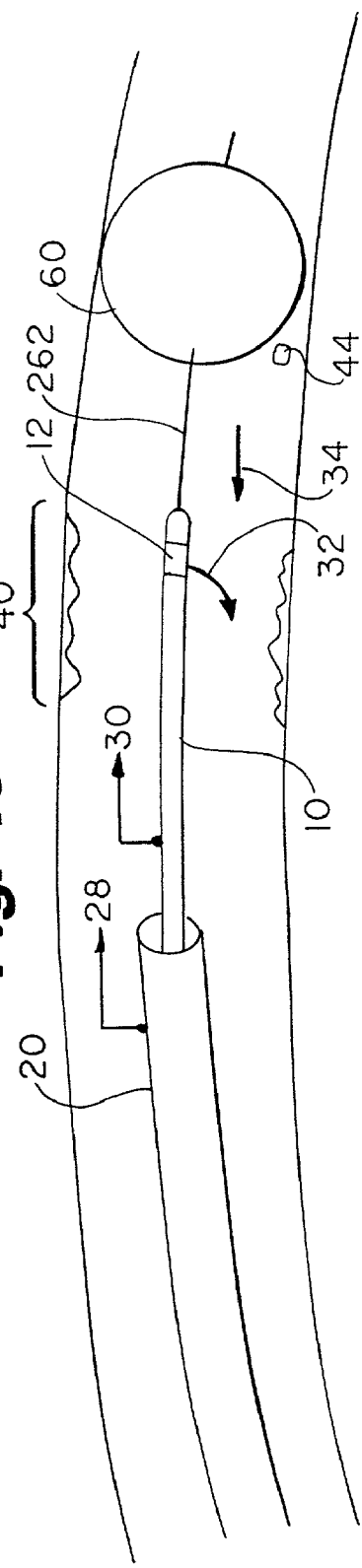

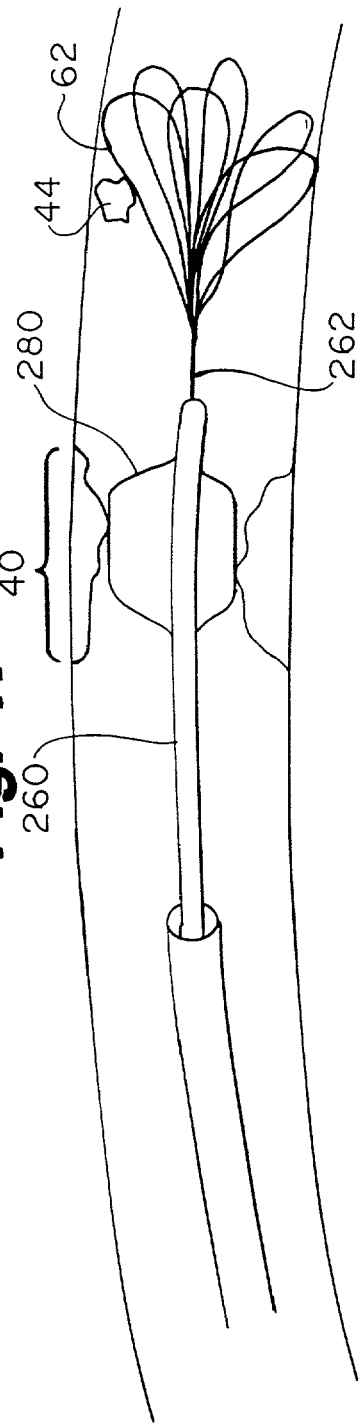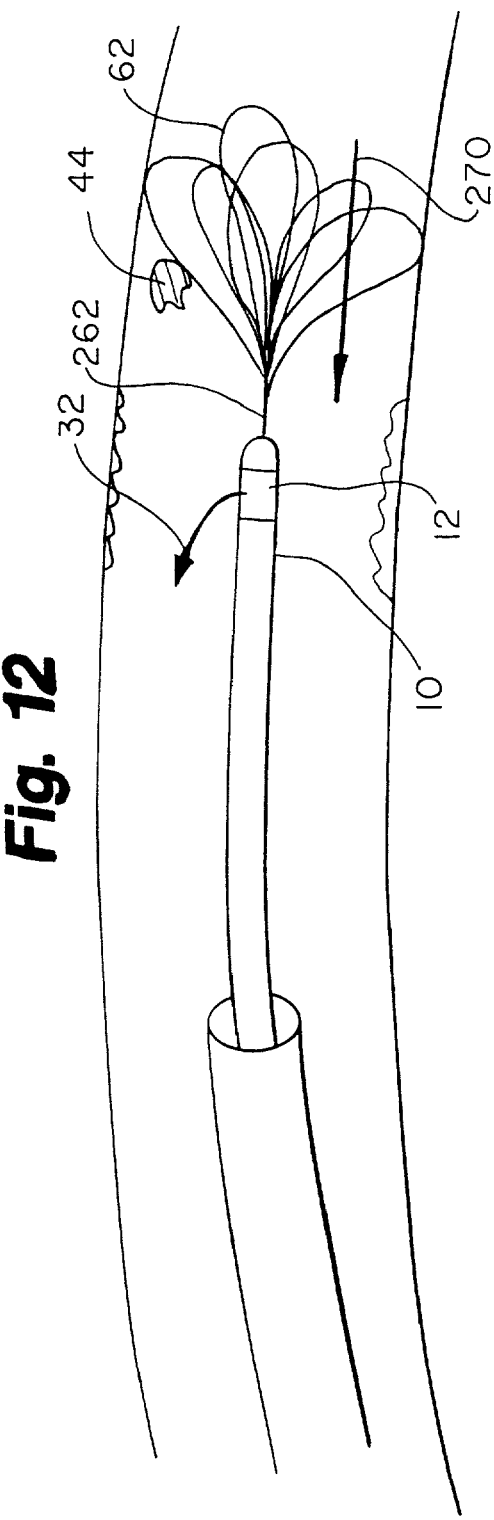

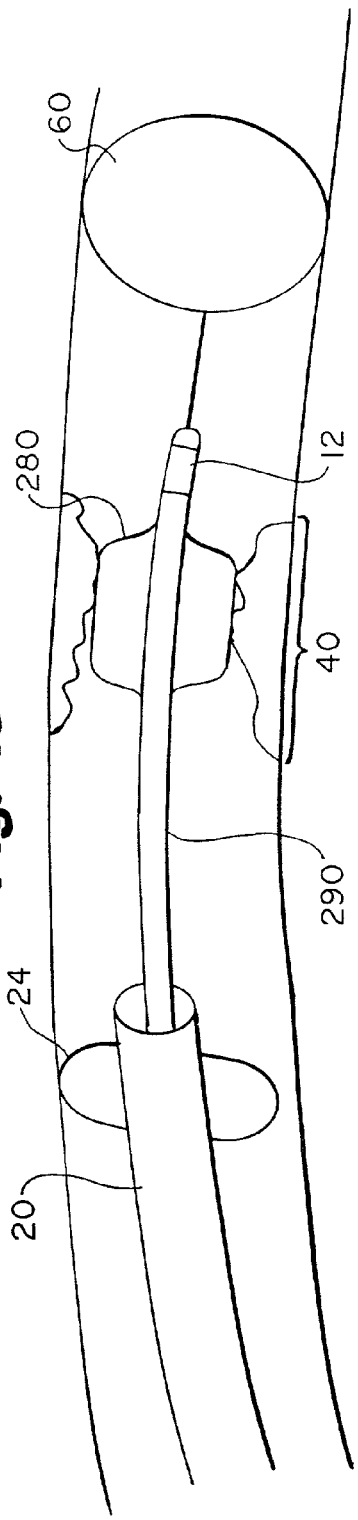
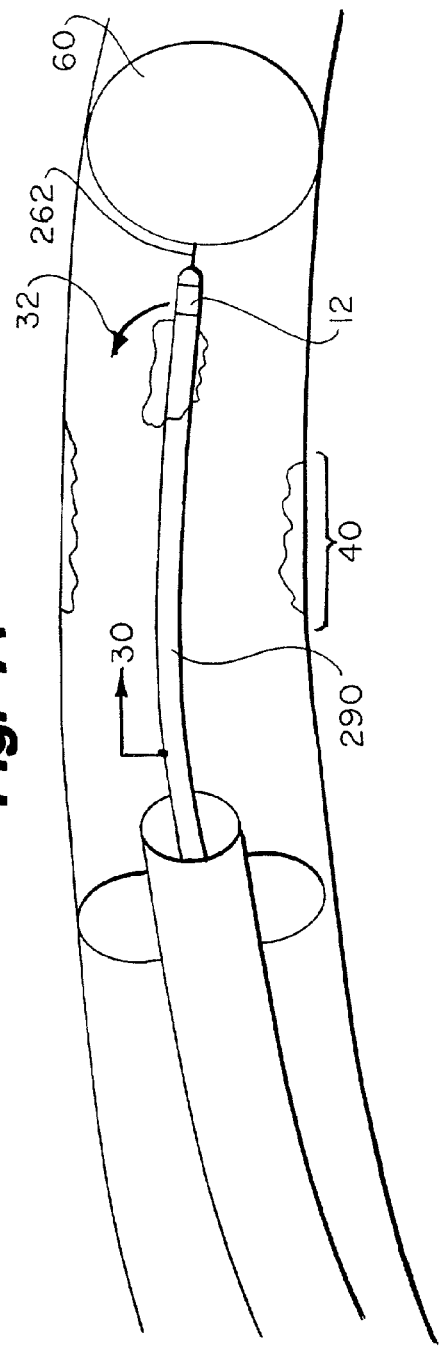

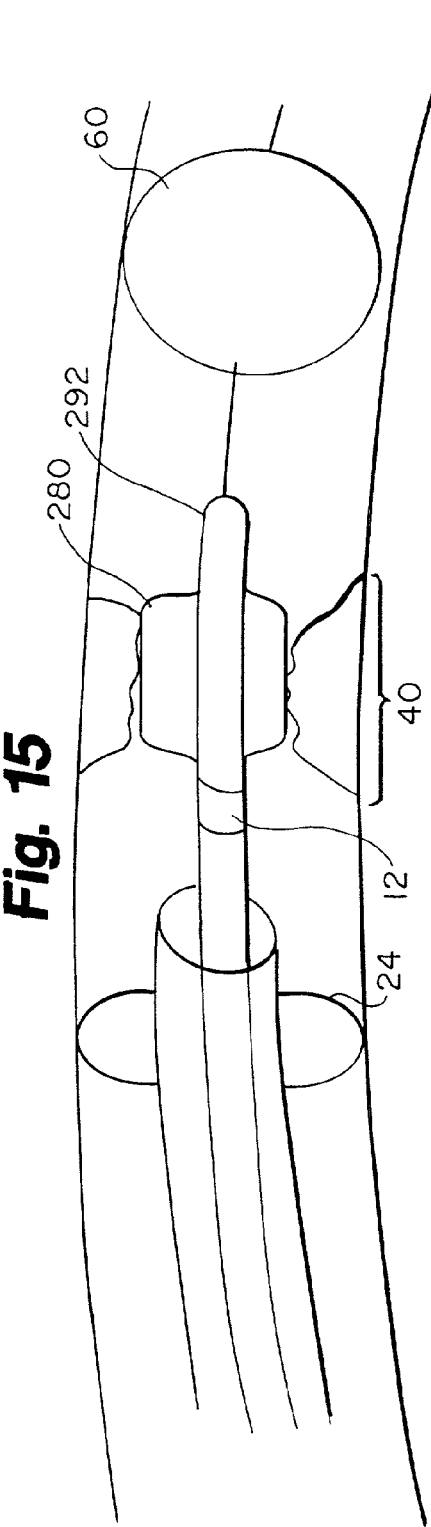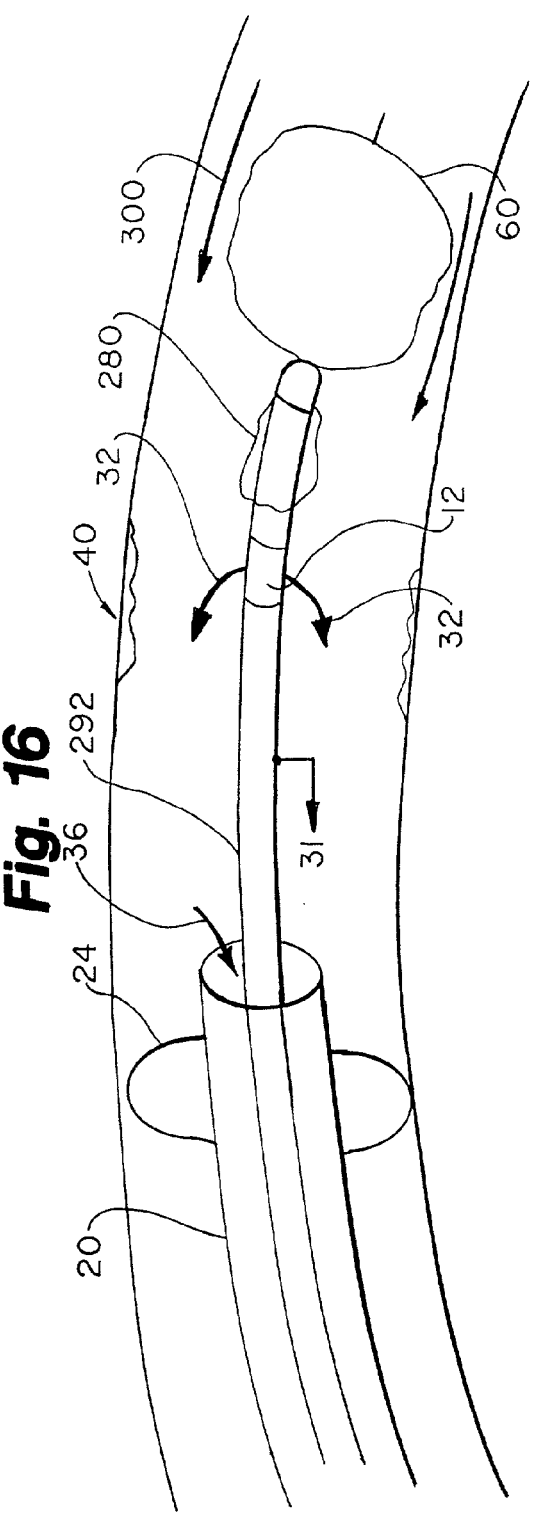

FLUIDIC INTERVENTIONAL DEVICE AND METHOD OF DISTAL PROTECTION

CROSS REFERENCE TO RELATED APPLICATIONS

This application is a Continuation-in-Part of U.S. patent application Ser. No. 09/995,303 filed Nov. 27, 2001 which is a Continuation of U.S. patent application Ser. No. 09/459,225 filed Dec. 10, 1999 now abandoned. The present application incorporates by reference these applications in their entirety.

This application is a Continuation-in-Part of U.S. patent application Ser. No. 09/637,529 filed Aug. 11, 2000 which is incorporated by reference in its entirety herein.

This application claims the benefit of U.S. Provisional Application Ser. No. 60/292,614 filed May 22, 2001 which is incorporated by reference in its entirety herein.

This application claims the benefit of U.S. Provisional Application Ser. No. 60/262,866 filed Jan. 18, 2001 which is incorporated by reference in its entirety herein.

This application claims the benefit of U.S. Provisional Application Ser. No. 60/293,856 filed May 25, 2001 which is incorporated by reference in its entirety herein.

This application claims the benefit of U.S. Provisional Application Ser. No. 60/296,592 filed Jun. 7, 2001 which is incorporated by reference in its entirety herein.

FIELD OF THE INVENTION

The present invention relates generally to a catheter for fluid delivery and aspiration, and more particularly to a device that utilizes the "wall attachment" or Coanda effect to interact with material in vessels or lumens of the body. In general the device will be used in the coronary arteries carotid arteries and the like.

In general, each embodiment of the device includes an "extraction section" which exhibits the wall attachment effect. The device may be used alone or with companion devices for thrombectomy, distal protection as well as other medical interventions.

BACKGROUND OF THE INVENTION

Fluid delivery and aspiration catheters are well known in the art. Catheter devices using the Coanda effect for various purposes are known as well. See for example U.S. Pat. No. 5,284,473 to Calabria and U.S. Pat. No. 5,344,395 to Whalen and Willard.

Specialized thrombectomy catheters, which rely on injected fluid to interact with occlusive material, are also know. U.S. Pat. No. 5,320,599 to Griep et al. appears to describe a device sold in the trade as the "Hydrolyzer." This device uses a "free" jet pointed in a retrograde direction to entrain ambient material in a blood vessel and to emulsify and propel this material out of the body.

Specialized distal protection devices are also known. See for example U.S. Pat. No. 6,135,991 to Ketan Muni, which describes the use of an occlusion device such as a balloon, to trap embolic particles released by a therapy such as angioplasty or the like. In operation the occlusion device is deployed proximal of a therapy device. After a therapy has been performed an aspiration catheter may be exchanged for the therapy catheter and debris removed from the location of the therapy by suction. It has also been suggested to use a rheolytic or Possis device with a balloon.

One problem with these prior art approaches is the inability to "see" the occlusion or treatment zone with contrast agent. The occlusion device prevents flow through the zone which forces the physician to work "blind" in the vessel.

SUMMARY

By way of contrast, contrast agent may be injected with my invention and the occlusions revealed during the procedure. In general, each embodiment of the device includes an extraction section that operates with a wall attachment effect. Fluid injected into the extraction section mixes with blood and occlusive material or debris in the body. The injected fluid is called the primary flow and the material which mixes with this primary flow is called the entrained flow. The mixing process may be quite vigorous and the energy represented by the primary pressurized fluid carries the entrained flow out of the body though a momentum exchange process.

This extraction section may operate alone or it may be combined with other therapeutic devices on the same catheter body. The extraction section may be used with other interventional device sections present on companion catheters.

For example, the extraction section may be combined with balloons for angioplasty and/or distal protection. The extraction section may be combined with other mechanical therapy deivces including rotating burrs and ultrasonic energy sources.

The invention is disclosed both in the context of the removal of blood thrombus and the removal of occlusive material liberated by a therapy such as angioplasty. The device may be used with occlusion devices and features such as balloons and filters. The device is also disclosed as a fluidic distal protection device, which induces a retrograde flow against normal arterial pressure.

In contrast to hydraulically powered catheters of the prior art which rely on one or more "free" jets the present invention relies on the wall attachment effect to produce a jet which interacts with and propels material from the body.

In general, the wall attachment effect takes place when a preferably annular sheet of fluid attaches to a wall after being injected at high pressure into a fluid medium. It is a property of such an attached flow that it may be "bent" to follow along the contour of the wall. The fluid discharge slit or gap and the wall surface to which it attaches form an asymmetrical jet geometry. Usually the jet is deflected through an angle as the wall turns through an angle. The attached jet sheds vortices which present a large and energetic surface area to entrain thrombus and other occlusive materials or other ambient fluids surrounding the primary jet.

In operation, the primary jet emerges from a preferably annular gap or slot and it attaches itself to a shoulder, nubbin or catheter wall surface. As the jet emerges from the gap, it spreads over the contour of the wall shoulder which gives the jet a greater working area. If a shroud, throat or vessel lumen is surrounding the jet, then excellent pressure recovery can be achieved which improves the overall extraction efficiency of the device. The device is scalable and it may serve as a guidewire or it may be delivered over a conventional guidewire or an occlusion type guidewire. It may be used alone as well.

The amount of energy available in the jet depends on both the injection pressure as well as the mass flow rate which are controllable within wide margins. If additional energy is required, the device may be combined and used in conjunction with a complimentary energy source such as ultrasonic energy or laser energy. The extraction section may thus be combined with a therapy section on the same catheter. The device may be delivered over a guidewire or through a procedure catheter or both may be used. The procedure catheter may become a portion of the system as well. The fluidic catheter may be moved with respect to the delivery catheter or delivery sheath, or it may be fixed with respect to the delivery sheath. Each alternative has special advantages.

In most embodiments the deflected fluid jet is substantially an annular sheet of fluid which becomes attached to the barrier wall. This jet sheds vortices which follow the wall for a distance as they exchange momentum with the surrounding fluids. The rotational and translational motion of the primary jet has substantially more energy than a conventional straight jet with the same input energy.

Various wall contours are within the scope of the invention. For example, a nubbin may form a wall that may grow in diameter measured from the slit in the retrograde direction. In a similar fashion the nubbin may decrease in diameter as measured from the slit in the retrograde direction. The wall may be cylindrical or undulating. In most versions of the device the primary fluid jet exits the catheter adjacent the wall in an approximately tangential fashion (0° to about 45°). In most embodiments the fluid jet will entrain ambient fluid on a continuous outer surface and this combined flow or stream is deflected through an angle which depends upon the initial energy in the jet and the wall contour. In most embodiments the deflection is about 90°. Other turning angles are contemplated as well including 0° embodiments where the flow attaches to the nubbin and is extracted by flowing into a lumen with essentially the same diameter as the nubbin.

In essentially all embodiments the jet presents a very large and energetic surface to entrain and emulsify occlusive material. Usually this entrainment surface is uniform and no net force is applied to deflect the catheter. However it is also possible to rely on asymmetric flow over the wall surface to steer the device while navigating it in a lumen or using it in a lumen.

In the most typical configuration the primary jet emerges from a generally annular gap which is approximately concentric with the body of the catheter. This jet is initially directed either outwardly from the central axis of the body in a radial direction varying from about 0° to 90° or along the central axis of the body at about 180°. After the flow attaches itself to a shoulder, nubbin or wall it follows that wall if the wall contour changes. As the jet emerges the relatively small nozzle area results in a substantial conversion of kinetic energy into momentum. That is, the high pressure in the jet blows down to arterial pressure or vessel pressure in a very short distance from the slit, thus both low pressure and high pressure versions of the device are safe for use in a vessel. For example discharge pressure of 100 psi or more do not result in vessel injury.

Typically the lower pressure versions operate as a pump while higher energy versions both pump and emulsify particulate occlusive material from vessels or lumens of the body. In contrast with other distal protection schema, the present invention uses a single device to both inject or irrigate the treatment site and the same fluid drives the debris out of the body.

BRIEF DESCRIPTION OF THE DRAWINGS

Throughout the figures like reference numeral indicate the same or similar structure wherein:

FIG. 9 is a schematic showing a method of use;
FIG. 10 is a schematic showing a method of use;
FIG. 11 is a schematic showing a method of use;
FIG. 12 is a schematic showing a method of use;
FIG. 13 is a schematic showing a method of use;
FIG. 14 is a schematic showing a method of use;
FIG. 15 is a schematic showing a method of use;
FIG. 16 is a schematic showing a method of use.

DETAILED DESCRIPTION

Overall System Architecture

FIG. 1 through FIG. 5 show several exemplary basic architectures for the fluidic interventional catheter system. In each figure, the system is shown within a blood vessel 25. In general the system is disclosed in the context of the treatment of coronary vessel disease and the system may be used in coronary arterial vessels of the heart and in saphanous veins harvested and implanted as coronary bypass vessels. The system may also be used in other vessels such as the carotids or other body lumens.

Figure 1:
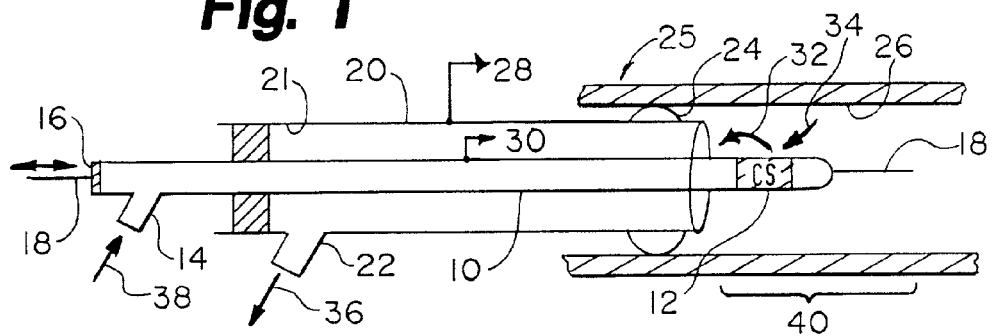
FIG. 1 is a schematic of device architecture.

The fluidic interventional catheter 10 shown in FIG. 1 has one extraction section 12 located near the distal tip of the catheter. At the proximal end of the catheter 10 there is a fluid injection port 14 for the injection of primary fluid. The fluid injection port is in fluid communication with the extraction section 12 at the distal tip. In this version of the fluidic catheter there is a guidewire port 16 located at the proximal end of the catheter 10 for using the catheter 10 with a conventional guidewire 18. Although an over-the-wire guidewire port is shown, rapid exchange or single operator exchange versions are contemplated within the scope of claims as well.

In FIG. 1 the catheter 10 is shown in an introducer sheath or guide catheter 20. The guide catheter or sheath 20 is shown with a port 22 for extracting entrained fluid at the proximal end of the sheath. An optional balloon structure 24 may be provided to seal the sheath 20 to the vessel lumen 26 or cavity. This balloon 24 is shown adjacent the distal end of the sheath 20. In most embodiments the sheath 20 and the catheter 10 are free to move with respect to each other as indicated by motion arrow 28 and motion arrow 30.

In operation, the extraction section 12 emits a primary fluid flow indicated by fluid arrow 32. Although this fluid will be ejected from all around the periphery of the catheter it is shown as a single flow emerging from one side of the extraction section 12 for clarity. It should be understood that the arrow 32 depicts the primary fluid regardless of jet angle or wall angle and is intended to depict generally the direction of flow and not the particular physics of any particular design. Ambient fluid near the extraction section 12 is entrained according to the wall attachment effect, and this entrained flow is indicated by fluid arrow 34. The combined flow exits the sheath through port 22 as indicated by flow arrow 36.

Thus, primary fluid injected into the catheter (depicted in the figure by fluid arrow 38) emerges from the extraction section 12 (depicted as flow 32) and interacts with ambient fluid (depicted as flow 34) resulting in a combined flow (depicted as flow 36) exiting the sheath at port 22. This convention is used though to depict the injected flow as 32 the entrained flow as 34 or 42 (depending on origin) and the combined flow as 36.

In this simple configuration the extraction section 12 interacts with the body at the treatment zone 40 in the vessel lumen 26. This architecture is useful for use with a standard guidewire 18. If a contrast enhancing fluid is injected into the device under substantial pressure the resulting vigorous jet emerging from the extraction section fills the vessel and reveals the shape of the occlusions in the treatment zone 40. Contrast agent can also be injected though the sheath lumen 21. This architecture is also useful for carotid protection during stenting where the fluidic intervention catheter 10 forces retrograde flow in a vessel during stenting in a companion vessel. Once again the injection of contrast agent permits the confirmation of retrograde flow.

Figure 2:
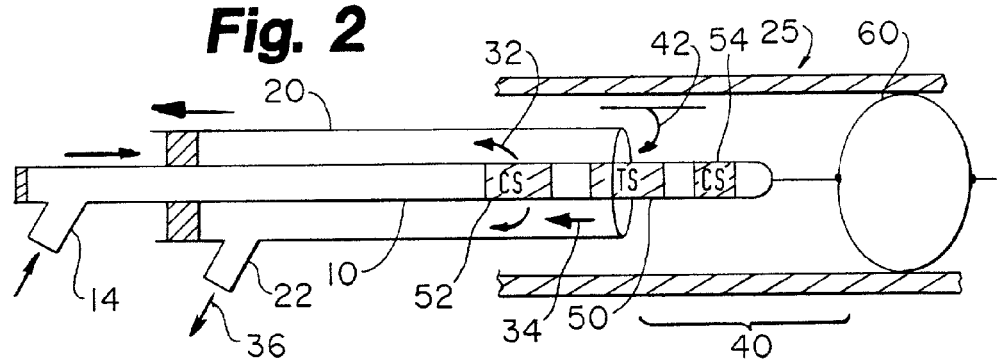
FIG. 2 is a schematic of device architecture.

FIG. 2 is an example of a system architecture which includes a therapy section 50 on the fluidic catheter 10. An extraction section 54 may be placed proximally of the therapy section 50 as illustrated. In the alternative the extraction section may be placed distally as indicated by extraction section 54. Each extraction section may be used alone or with an optional companion extraction section.

This figure serves to illustrate several contemplated embodiments. These embodiments include devices with extraction sections both proximal and distal of a single therapy section as well as devices with a single extraction section proximal of a therapy section and devices with an extraction section proximal of a therapy section. Also illustrated are devices with multiple therapy sections and multiple extraction sections.

As seen in FIG. 2, the extraction section 52 is located within the sheath 20. This extraction section operates as a pump with the retrograde flow 32 inducing a secondary entrained flow 34 which extracts ambient fluid 42 from the treatment zone 40. As indicated in the figure, the extraction section 12 may promote flow of fluid from the retrograde direction as indicated by the direction of flow arrow 42. However, it should be understood that the extraction section could be reversed in direction and used to inject fluid in the antegrade direction as well.

In this particular figure a balloon occlusion device 60 is shown deployed from the guidewire lumen of the device 10. Occlusion devices such as the Medtronic AVE "Guardwire" are available to close off vessels by inflating a balloon. Alternate occlusion devices include filters which may be deployed in the same location. An example of a filter type occlusion device is the "Angiogard" wire is currently undergoing clinical testing.

The term "occlusion device" encompasses both total occlusion devices such as occlusion balloons 60 and filter type occlusion devices 62. In the figures one may substitute one form of occlusion device for the other in most instances with only minor modification of the interventional procedure. If a total occlusion device such as a balloon 60 is used the entrained flow may come from the area of the balloon or it may come from the area between the outside of the sheath 20 and the lumen 26 of the vessel or both locations as indicated by flow arrow 42. One should note that in FIG. 2 there is no balloon sealing the sheath or guide catheter so coronary blood flow is available to be drawn into the lumen of the sheath 20 by the pumping action of the extraction section 52. This incoming flow 42 replaces fluid ejected from the extraction section 52 depicted by flow arrow 32. The two extraction sections 54 and 52 may be operated together or separately.

Figure 3:
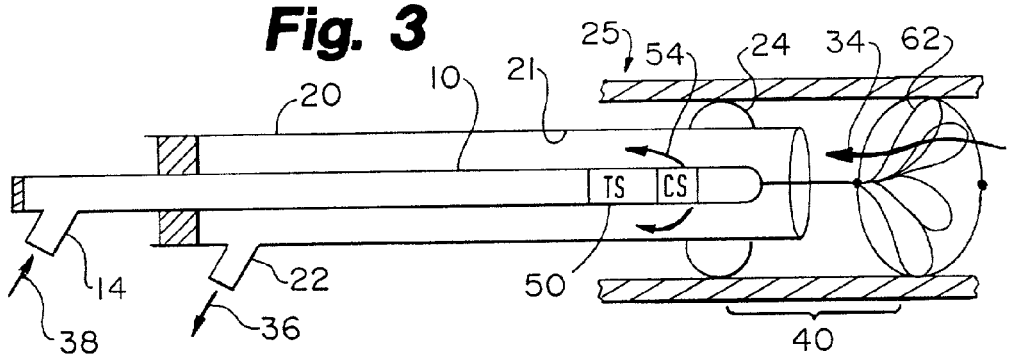
FIG. 3 is a schematic of device architecture.

FIG. 3 shows a fluidic catheter 10 located directly adjacent a therapy section 50. Here the extraction section 54 can be used as a pump for removing debris from a filter type occlusion device 62. In this particular embodiment a balloon 24 on the sheath is inflated to seal off the vessel so that the bulk of the entrained flow 34 is drawn directly from and through the occlusion device shown as a filter 62. In this architecture, the fluidic catheter and its extraction section 54 are used in connection with a treatment section 50 to treat the treatment zone 40 and to remove debris created by that treatment. An example of a treatment section 50 useful in this architecture is an angioplasty balloon or a stent placement balloon. It must also be recognized that the balloon 24 may not be required. This is especially true if the extraction section 54 is located within the sheath 20 and is shrouded by the lumen 21 as shown in the figure.

Figure 4:
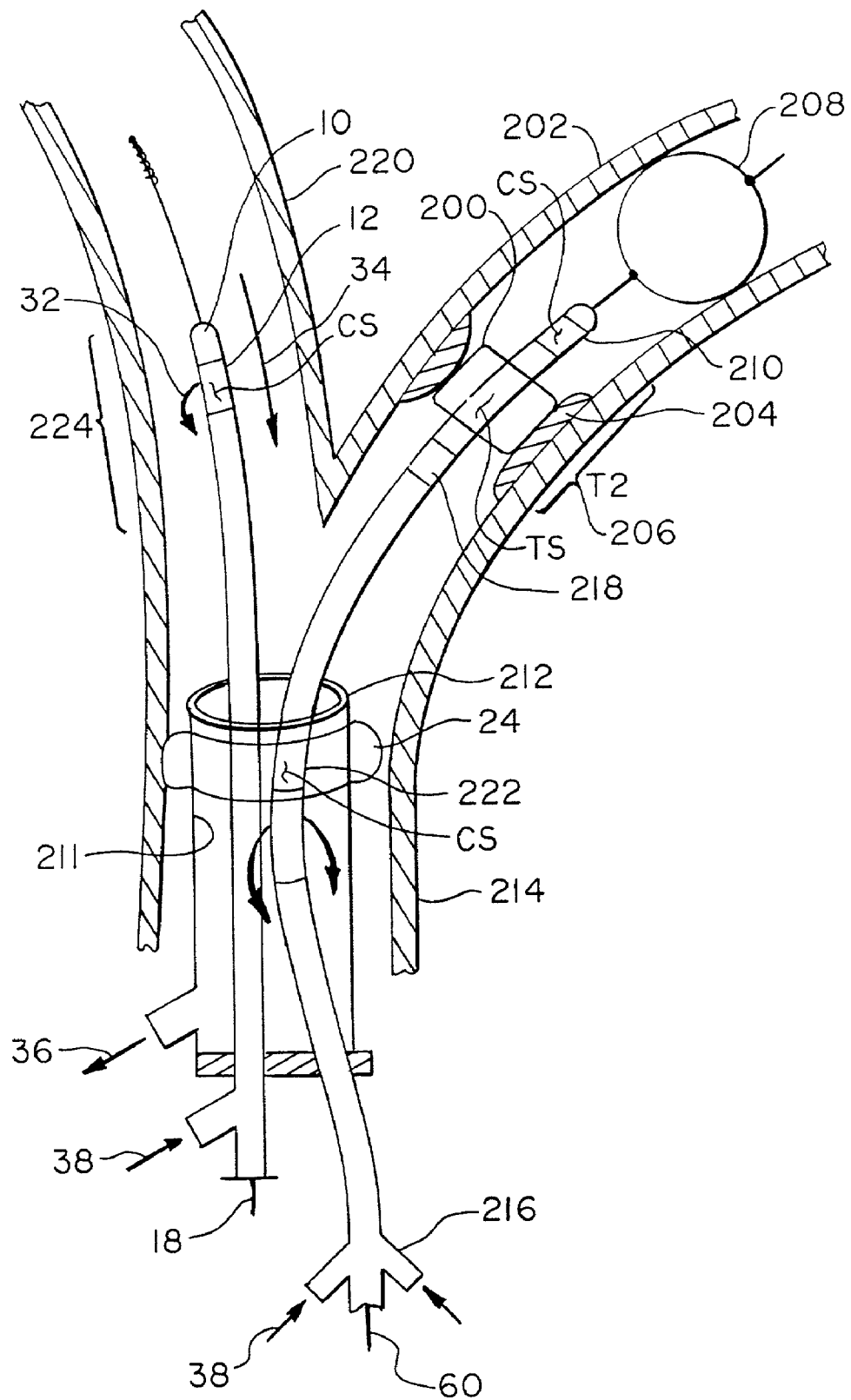
FIG. 4 is a schematic of device architecture.

FIG. 4 shows an alternate architecture where a fluidic catheter 10 is being used to provide hydraulic distal protection in one branch of a bifurcation while a therapy is proceeding in an adjacent vessel. In the figure a balloon 200 is being used in the internal carotid 202 to treat a lesion 204 in a treatment zone 206. An occlusion device 208 is placed distal of the lesion and it blocks the flow of particulates downstream toward the brain. After the balloon 208 is deflated the extraction section 210 will be activated to propel debris toward the open lumen 211 of the sheath 212 located in the common carotid 214. An auxiliary extraction section 218 proximal of the treatment balloon 200 may be used to assist in clearing the vessel.

The sheath 212 may have an optional balloon 24 to seal the common carotid during the intervention. When the balloon is deflated though port 216 the physician will activate both the extraction section 210 carried on the balloon therapy device while activating the extraction section 12 on the device 10 located in the external carotid 220. The primary flow forces the combined flow 36 into the open lumen of the sheath 212. This fluidic jet 32 and associated flow 34 provides a protected zone 224 in the companion vessel 220 which prevents the debris from the treatment zone 206 from entering the external carotid 220. This strategy is especially useful when the balloon 24 is deflated or not present. In this case the blood flow from the common carotid can enter the external carotid until the physician actives the extraction section 12 on the device 10 which then temporally reverses flow in the vessel.

An auxiliary extraction section 222 may be placed in the open lumen 211 of the sheath 212 to eject debris from the body.

Figure 5:
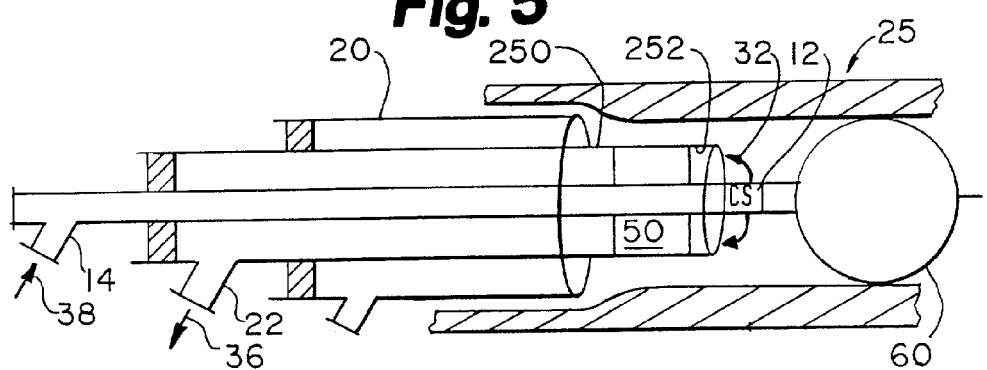
FIG. 5 is a schematic of device architecture.

FIG. 5 shows an extraction section 12 combined with a distal protection device of the balloon type. In this embodiment an occlusion filter may be substituted for the balloon. In FIG. 5 the therapy section 50 is on a separate catheter 250 that incorporates an extraction lumen 252. In use, after the therapeutic intervention the therapy catheter 250 is advanced toward the occlusion balloon 60 and the majority of the entrained flow will exit the therapy catheter as depicted by flow 36. This flow is propelled by the extraction section 12 operating in the vessel and then operating in the lumen 252.

In summary, the extraction section may be used alone or combined with a therapy device. More specifically the extraction section may reside on an angioplasty catheter, or a distal protection catheter or it may be used alone in the vessel or catheter lumen.

The Extraction Section Geometry

The extraction section 12 may take any one of several forms. In the figures the extraction sections may take the form of FIG. 6 or FIG. 7. The FIG. 8 embodiments would require complimentary changes to be used in the architectures depicted in FIGS. 1-5.

In general all embodiments rely on the wall attachment effect which is sometimes called the Coanda effect. Wall attachment occurs when the injected fluid emerges near a wall or barrier and begins to entrain ambient fluid. The entrainment process causes the emerging jet to be pushed against the wall. Once the emerging jet is attached to the wall it will follow the wall contour for a long distance. The geometry of the extraction section is quite flexible and numerous geometric combinations will exhibit a useful wall attachment effect.

To define the extraction section it is useful to first define certain axises and angles. First, there is a geometric axis for the fluid as it emerges from the fluid supply lumen called "jet axis". This axis is defined as the direction that the jet squirts when the device is operated in air. This may be tested by suspending the device in air and injecting distilled water into the device.

The long length of the catheter body will carry the fluid supply lumen and the fluid supply lumen has a "lumen axis". The body of the catheter has a "body axis". In most instances the body axis is parallel to the supply "lumen axis".

The angle between the body axis and the jet axis is the "jet angle" measured from the body axis as seen in figures and labeled JA in the figures. This JA angle may vary from about 90 degrees where the jet is directed directly radially from the body through 180 degrees where the geometric axis points in the proximal or retrograde direction. Beyond 180 degrees the nozzle becomes "internal" as described in FIG. 8.

The wall or barrier is located proximate the jet and it forms an angle with respect to the geometric jet axis or JA. This wall angle WA can vary from about 0 degrees where the jet axis is both tangent and parallel to the wall to about 45 degrees or more. As the wall angle WA increases from 0 to 45 degrees or more it take more time for the jet to attach to the wall after the jet emerges. However the jet, once attached is stable and the turbulence and vorticity is very large. As the jet angle decreases from about 180 degrees to about 90 degrees the effective diameter of the entrained flow increases and the turbulence increases.

Details of construction may vary widely and are known to those of ordinary skill in this art. When the flow rates are low, multiple individual lumens may be use to supply fluid to a distal cap area. A slit or gap may be provided to provide an exit for the fluid and it may directed at any convenient "jet angle". The attachment wall or surface may be formed by a separate bead or nubbin placed near the slit or gap. A single annular slit or gap is preferred but a number of individual jets may be used as well. In general the wall angle must be reduced to get good attachment with individual jets. If the jet angle is about 135 degrees the catheter body itself may form the attachment wall. The problem with individual jets is that the "edges" of the jets allow for ventilation of the underside of the jet.

Figure 6:
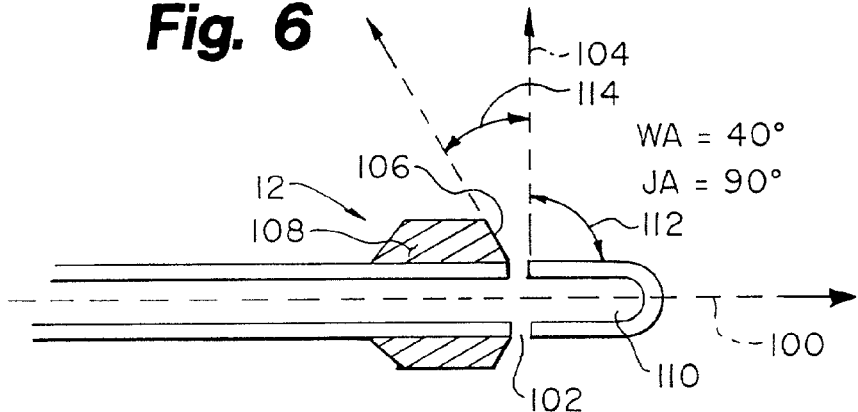
FIG. 6 is a schematic of the extraction section geometry.
Figure 7:
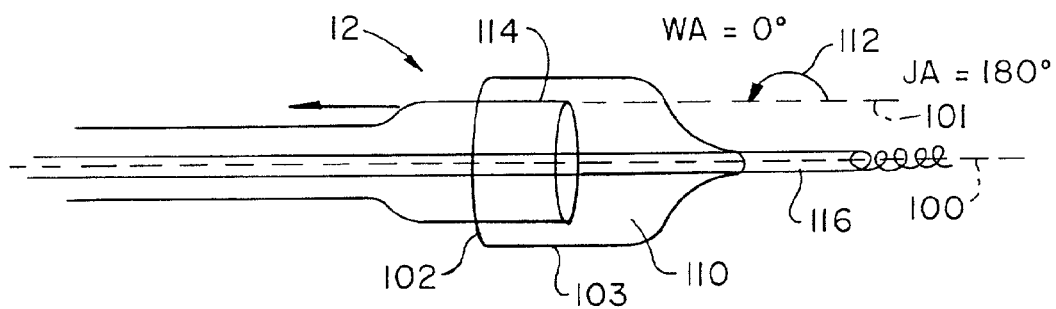
FIG. 7 is a schematic of the extraction section geometry.
Figure 8:
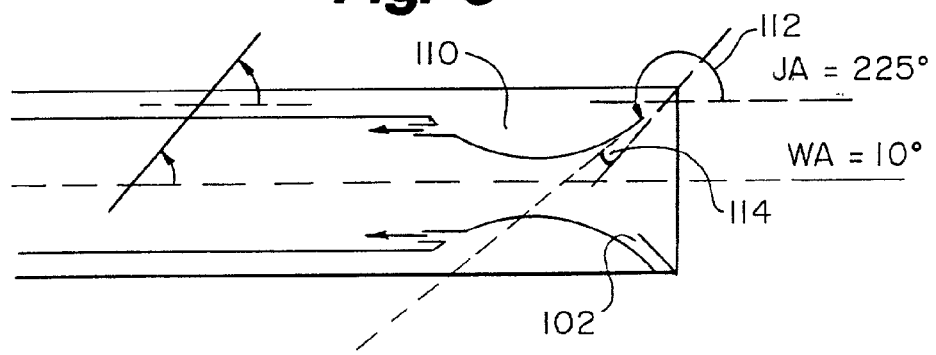
FIG. 8 is a schematic of the extraction section geometry.

When the jet angle is extended beyond 180 to approximately 225 degrees the wall attachment nozzle goes from "external" as seen in FIGS. 6 and 7 to "internal" as seen in FIG. 8.

Experimentation has shown that a small enlargement of the supply lumen adjacent to the fluid supply gap improves the stability of the attached jet. This navicular fossa 110 region seems to promote stable attachment of the jet to the wall. A suitable location for this volume is identified with ref numeral 110 in each of FIGS. 6 7 and 8.

FIG. 6 FIG. 7 and FIG. 8 should be considered together as they show the development of variations of the wall attachment jet geometry for the extraction section of the catheter.

In FIG. 6 the catheter body and the single lumen share the same axis 100. A slit or series of slits surround the catheter body forming exit jet apertures typified by jet aperture 102. When operated in air the fluid emerging from the jet apertures flows a path indicated by arrow 104. This jet direction is used to defined the "jet angle" 112 on the figure, It is measured counterclockwise from the catheter axis 100 and is approximately 90 degrees in FIG. 6. The conical wall 106 is placed near the jet aperture 102 and the angle tangent to the wall measured toward the jet direction or JA is the "wall angle" or WA 114. In this figure the wall angle is about 40 degrees. In operation, the fluid starts out in the jet direction and attaches to and follows the contour of the nubbin 108. FIG. 6 is an example of an extraction section 12 with a jet angle of about 90 degrees and a wall angle of about 40 degrees.

In FIG. 7 the catheter body and the fluid supply lumen share the same direction 101. In this configuration the jet angle 112 is increased to 180 degrees and it points directly rearward in the sense of the figure. In this particular design the guidewire lumen 116 tube provides a convenient location to bond the over-tube 103 which forms the gap or slit 102. This nozzle represents an extraction section 12 with a jet angle of 180 degrees and a wall angle of 0 degrees.

In FIG. 8 the nozzle has been turned inside out and forms an internal rather than external nozzle. In this geometry the jet angle has been increased to 225 degrees and now points inward. The wall angle is about 10 degrees. A set of auxiliary jets typified by jet 118 can be provided as well. It too achieves wall attachment on the internal surfaces of the device.

Exemplary Methods of Use

FIG. 9 depicts a method of use for a simple fluidic interventional catheter 10 used in conjunction with a balloon angioplasty procedure. In this particular example a balloon 60 occlusion device is first advanced into the vessel past the treatment zone 40. Next, the balloon catheter 260 is inflated to treat the lesion in the treatment zone by expanding the balloon 280 into the lesion.

Next, the treatment catheter 260 is removed and a fluidic catheter 10 is guided to the treatment zone 40 along the occlusion wire 262 as depicted in FIG. 10. Primary fluid 32 which may be radiopaque or normal saline is injected in to the extraction section 12 and the entrained flow 34 is propelled out of the lumen of the sheath 20. The sheath may be fixed and the catheter moved toward the balloon 60 as indicated by arrow 30. In the alternative the sheath may be advanced toward the balloon 60 as indicated by arrow 28. It is also desirable in some instances to advance both the sheath 20 and the device 10 simultaneously or sequentially. The balloon 60 may be deflated preferably after the primary flow 32 is turned on. By deflating the balloon 60 after the primary flow is injected particulate typified by particle 44 at the periphery of the balloon will be entrained into the sheath 20 which is desirable.

FIG. 11 depicts a method of use for a simple fluidic interventional catheter 10 used in conjunction with a conventional balloon angioplasty procedure. In this particular example a filter 62 type distal occlusion device is placed in the vessel lumen. The occlusion device 62 is first advanced into the vessel past the treatment zone 40 and deployed to collect debris typified by particle 44.

Next, the balloon catheter 260 is inflated to treat the lesion in the treatment zone 40. The balloon 280 inflates and opens the vessel.

In FIG. 12 the treatment catheter 260 is removed and a fluidic catheter 10 is guided to the treatment zone along the occlusion wire 262. Primary fluid 32 which may be radiopaque or normal saline is injected by the extraction section 12 on the device 10 and the entrained flow is propelled out of the lumen of the sheath 20. The sheath may be fixed and the catheter moved toward the balloon 60. In the alternative the sheath may be advanced toward the filter 62. It is also desirable in some instances to advance both the sheath 20 and the device 10 simultaneously or sequentially. The filter 62 allows blood and debris to be pumped "backwards" into the sheath as indicated by flow 270.

In general filter type devices are useful but they can clog with too much debris which makes removal problematic. In this system the catheter 10 can empty the filter 62 and clear debris 44 before the filter device 62 is removed.

FIG. 13 depicts a method of use for a combined therapy and fluidic interventional catheter 290 used in conjunction with a balloon angioplasty procedure. In this particular example a balloon 60 type distal occlusion device is placed in the vessel lumen. The occlusion device 60 is first advanced into the vessel past the treatment zone 40 and deployed to collect debris released by the procedure.

Next, the combined fluidic and balloon catheter 290 is inflated to treat the lesion in the treatment zone 40. The balloon 280 inflates and opens the vessel.

Next, the extraction section 12 which is carried on the catheter and placed distal of the balloon 280 is activated while the balloon is deflated. It is preferable to activate the extraction section 12 after the catheter is advance toward the occlusion device as indicated by arrow 30. In this intervention the balloon 24 on the sheath 20 is inflated at least during the debris recovery process.

Alternatively, the balloon 280 may be deflated and the device 290 reciprocated several times up and down the wire 262 to clear debris from the treatment zone.

FIG. 15 depicts a method of use for a combined therapy and fluidic interventional catheter 292 used in conjunction with a balloon angioplasty procedure. In this particular example a balloon 60 type distal occlusion device is placed in the vessel lumen. The occlusion device 60 is first advanced into the vessel past the treatment zone 40 and deployed to collect debris released by the procedure.

Next, the combined fluidic and balloon catheter 292 is inflated to treat the lesion in the treatment zone 40. The balloon 280 inflates and opens the vessel.

Next, the extraction section 12 which is carried on the catheter and placed proximal of the balloon 280 is activated while the balloon is deflated. It is preferable to activate the extraction section 12 after the catheter is advance toward the occlusion device. It may also be used while moving away from the occlusion balloon. as indicated by arrow 31. In this intervention the balloon 24 on the sheath 20 is inflated at least during the debris recovery process.

It should be noted that the deflation of the occlusion balloon 60 will result in retrograde flow as indicated by arrow 300. When the extraction section 12 is operating the primary flow 32 entrains the blood 300 and forces the entire flow 36 into the sheath 20.

Figure 17:
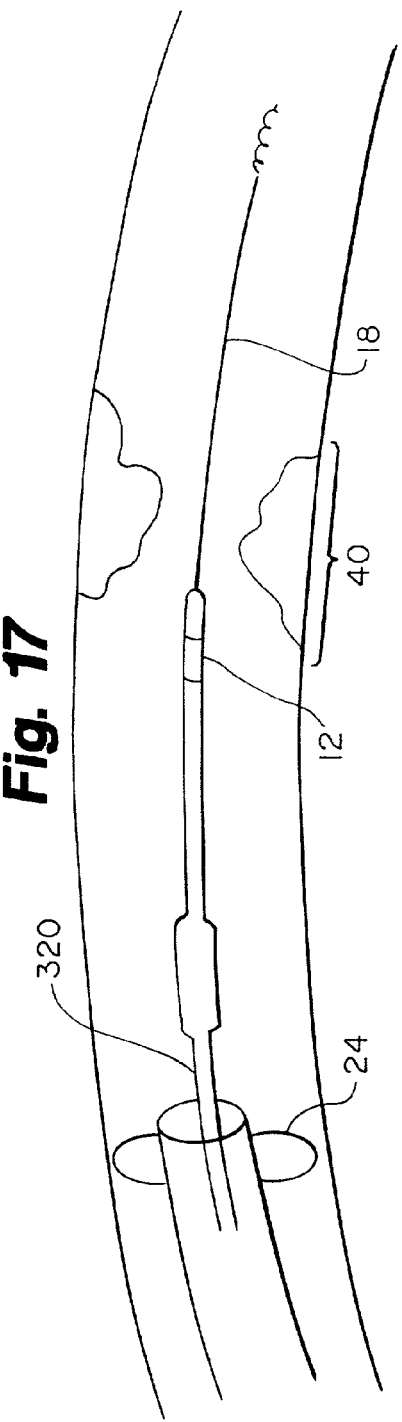
FIG. 17 is a schematic showing a method of use.

FIG. 17 depicts a combination catheter 320 with a balloon treatment section having balloon 280 and relatively long proximal "snout" with an extraction section 12 located near its tip. In use, the conventional guidewire 18 is used to traverse the lesion in the treatment zone 40 and the combination catheter is moved into position to treat the lesion.

Figure 18:
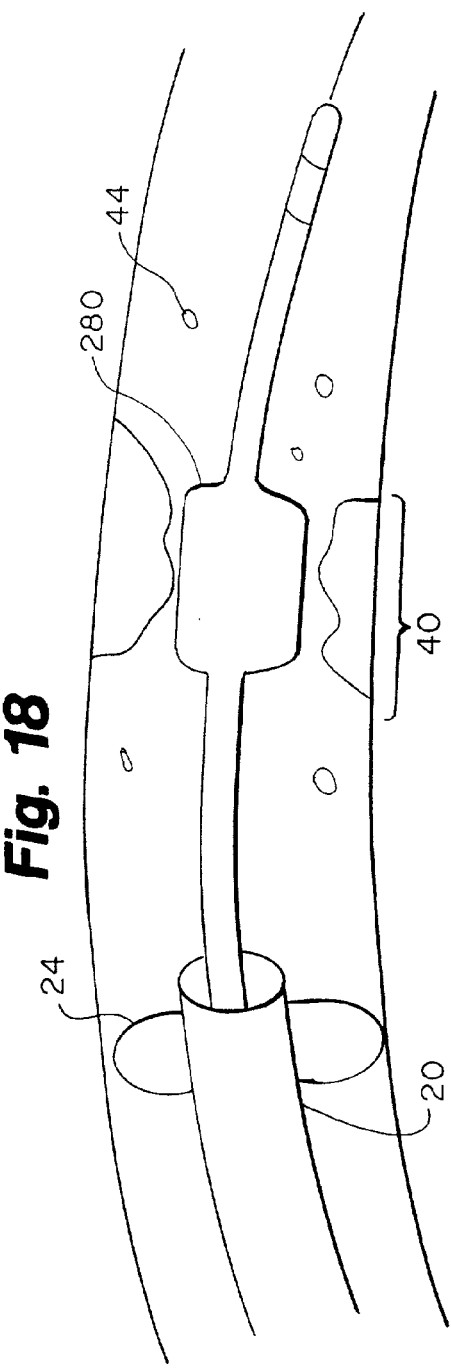
FIG. 18 is a schematic showing a method of use; and,
FIG. 19 is a schematic showing a method of use.

FIG. 18 shows the combination catheter 320 in position with the balloon 280 inflated to remodel the plaque in the lesion. This process liberates debris typified by particle 44. Since the vessel is occluded by the sheath balloon 24 and by closing off the central lumen of the sheath 20 the particles and other debris will not move very far downstream.

Figure 19:
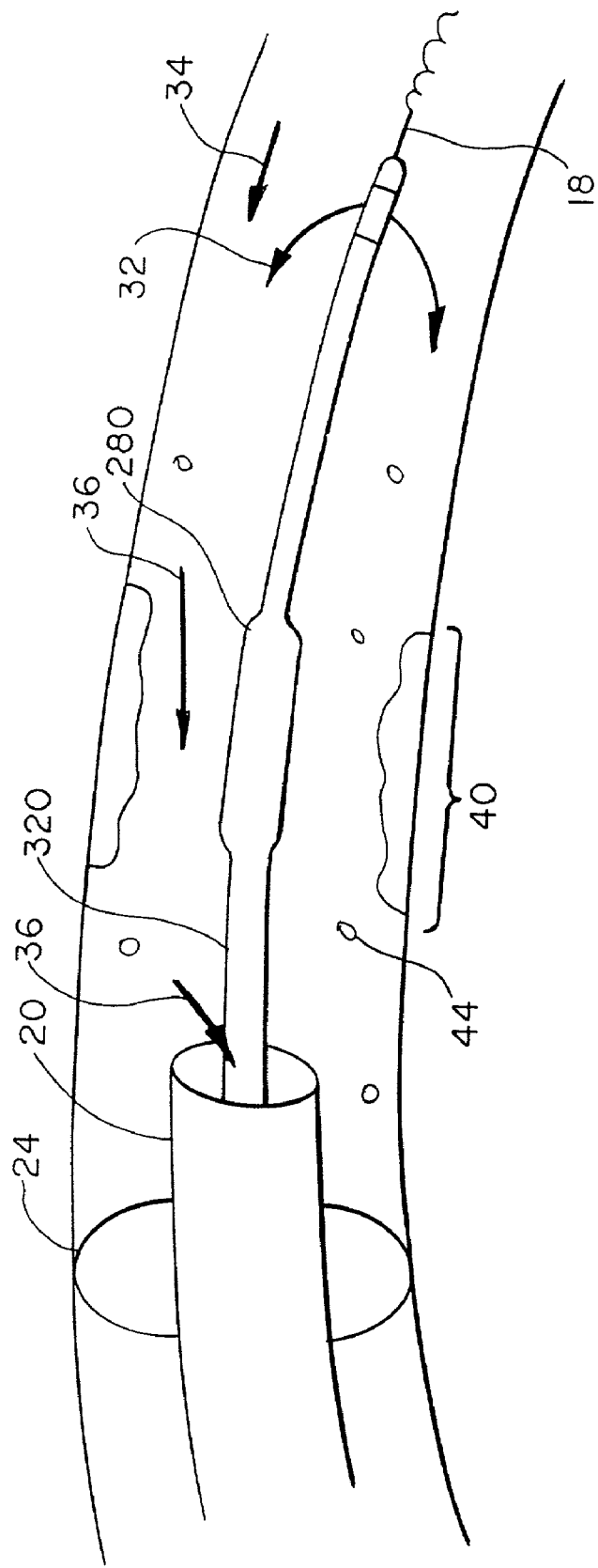

FIG. 19 shows the balloon 280 being deflated as the primary fluid 32 is injected. The induced retrograde flow 36 sweeps the loose particulate into the open lumen of the sheath 20 providing a completely hydraulic form of distal protection.

In use the catheter 320 can be withdrawn into the sheath to completely remove particulate liberated by the angioplasty process.

What is claimed is:

1. A method of providing embolic protection at a lesion in a treatment zone in a vessel, the lesion location defining the location of the treatment zone, said method comprising:
   inserting and positioning an occlusion device in said vessel at a location distal of the lesion without placing an occlusion device proximal of the lesion in the same vessel;
   treating a lesion is said vessel at a treatment zone near said occlusion device with a treatment device; followed by,
   positioning an extraction section at a location near said lesion, said extraction section of the type having a fluid ejection port where injected primary fluid mixes with ambient fluid and debris creating a wall attached entrained flow;
   supplying a fluid to said extraction section forming a primary flow to engage and entrain debris at the site of said lesion generating an entrained flow, said entrained flow containing both primary flow and debris from the lesion;
   providing a sheath having an extraction lumen proximal of said extraction section to receive said entrained flow.

2. The method of claim 1 wherein:
   said sheath extraction lumen is advanced alternately toward said extraction section and away from said extraction section to further extract debris while said extraction section is approximately stationary in said vessel.

3. The method of claim 1 wherein:
   said extraction section 12 is alternately advanced toward said occlusion device and away from said occlusion device while said extraction sheath lumen remains relatively stationary in said vessel to further extract debris.

4. The method of claim 1 wherein:
   said occlusion device is an inflatable balloon.

5. The method of claim 4 wherein:
   said supplying step occurs while the occlusion device is deflated after the therapeutic intervention of the lesion.

6. The method of claim 1 wherein:
   said occlusion device is an occlusion filter.

7. The method of claim 5 wherein:
   said supplying step occurs during the occlusion device deflation after the therapeutic intervention of the lesion.

8. The method of claim 5 wherein:
   said supplying step occurs prior to the occlusion device deflation after the therapeutic intervention of the lesion.

9. The method of claim 1 wherein:
   said extraction section has a jet angle of approximately ninety degrees, and a wall angle of approximately forty degrees.

10. The method of claim 1 wherein:
    said extraction section has a jet angle of approximately one hundred eighty degrees, and a wall angle of approximately zero degrees.

11. The method of claim 1 wherein:
    said extraction section has a jet angle between approximately one hundred eighty degrees and ninety degrees, and a wall angle of between approximately zero degrees and forty-five degrees.

12. A method of embolic protection at a lesion in a treatment zone in a vessel comprising:
    introducing a sheath having an occlusion balloon and an extraction lumen to a location proximal of said lesion;
    inflating said occlusion balloon;
    introducing an angioplasty catheter having an extraction section distal of said therapy balloon into a vessel said extraction section of the type having a fluid ejection port where injected primary fluid mixes with ambient fluid and debris creating a wall attached entrained flow;

inflating the therapy balloon to treat the lesion;

activating the extraction section by injecting primary fluid under pressure;

deflating the therapy balloon;

allowing or causing a retrograde flow to remove debris from treatment zone through said extraction lumen.

13. A method of embolic protection at a lesion in a treatment zone in a vessel comprising:

introducing a sheath having an occlusion balloon and an extraction lumen to a location proximal of said lesion;

inflating said occlusion balloon;

introducing an angioplasty catheter having an extraction section said extraction section of the type having a fluid ejection port where injected primary fluid mixes with ambient fluid and debris creating a wall attachment entrained flow, distal of said therapy balloon into a vessel;

activating the extraction section by injecting primary fluid under pressure;

inflating the therapy balloon to treat the lesion;

deflating the therapy balloon;

allowing or causing a retrograde flow to remove debris from treatment zone through said extraction lumen.

14. A method of providing embolic protection at a lesion in a treatment zone in a vessel, the lesion location defining the location of the treatment zone, said method comprising:

inserting and positioning an occlusion device in said vessel at a location distal of the lesion or proximal of the lesion but not both proximal and distal of the lesion in the same vessel;

positioning an extraction section of the type having a fluid ejection port where injected primary fluid mixes with ambient fluid and debris creating a wall attachment entrained flow, at a location near said lesion distal of a therapy section on a single catheter, followed by;

treating a lesion is said vessel at a treatment zone near said occlusion device with said treatment section;

supplying a fluid to said extraction section forming a primary flow to engage and entrain debris at the site of said lesion generating a wall attachment entrained flow, said entrained flow containing both primary flow and debris from the lesion;

providing a sheath having an extraction lumen proximal of said extraction section to receive said entrained flow.

15. The method of claim 14 wherein:

said therapy section is an angioplasty balloon and the supplying step occurs while the angioplasty balloon is deflated.

16. The method of claim 14 wherein:

said therapy section is an angioplasty balloon and the supplying step occurs prior to and during the deflation of the angioplasty balloon.

17. The method of claim 14 wherein:

said occlusion device is a balloon located on the distal end of said sheath.

* * * * *